US011351346B2

(12) United States Patent
Tummala et al.

(10) Patent No.: US 11,351,346 B2
(45) Date of Patent: Jun. 7, 2022

(54) BALLOON SHEATH AND ASSOCIATED METHODS

(71) Applicants: Venkat Tummala, Lakeland, FL (US); Fakhir F. Elmasri, Lakeland, FL (US)

(72) Inventors: Venkat Tummala, Lakeland, FL (US); Fakhir F. Elmasri, Lakeland, FL (US)

( * ) Notice: Subject to any disclaimer, the term of this patent is extended or adjusted under 35 U.S.C. 154(b) by 0 days.

(21) Appl. No.: 16/169,565

(22) Filed: Oct. 24, 2018

(65) Prior Publication Data

US 2019/0262590 A1 Aug. 29, 2019

Related U.S. Application Data

(60) Provisional application No. 62/576,147, filed on Oct. 24, 2017.

(51) Int. Cl.
*A61M 25/10* (2013.01)
*A61B 17/22* (2006.01)
*A61B 17/3207* (2006.01)
*A61B 17/30* (2006.01)

(52) U.S. Cl.
CPC ........... *A61M 25/104* (2013.01); *A61B 17/22* (2013.01); *A61M 25/10184* (2013.11); *A61B 2017/22048* (2013.01); *A61B 2017/22067* (2013.01); *A61B 2017/22079* (2013.01); *A61B 2017/306* (2013.01); *A61B 2017/320716* (2013.01); *A61M 2025/109* (2013.01); *A61M 2025/1081* (2013.01); *A61M 2025/1093* (2013.01)

(58) Field of Classification Search
CPC ........... A61B 2017/22051; A61B 2017/22079; A61B 17/12022; A61B 2017/00576; A61B 2017/12136; A61M 2025/1052; A61M 2025/0024; A61M 25/10; A61M 25/10184; A61F 2/016
See application file for complete search history.

(56) References Cited

U.S. PATENT DOCUMENTS

| | | | |
|---|---|---|---|
| 6,022,336 A * | 2/2000 | Zadno-Azizi | A61B 17/22 604/101.05 |
| 6,083,255 A * | 7/2000 | Laufer | A61B 18/00 607/101 |
| 6,379,365 B1 | 4/2002 | Diaz | |
| 6,511,492 B1 | 1/2003 | Rosenbluth et al. | |
| 7,524,303 B1 | 4/2009 | Michael et al. | |
| 8,075,510 B2 | 12/2011 | Aklog et al. | |
| 8,348,889 B2 | 1/2013 | Salemi et al. | |
| 8,858,490 B2 | 10/2014 | Chou et al. | |
| 9,987,025 B2 | 6/2018 | Becker | |
| 2004/0243175 A1 | 12/2004 | Michael | |
| 2005/0228402 A1 | 10/2005 | Hofmann | |
| 2013/0304082 A1* | 11/2013 | Aklog | A61B 17/3207 606/127 |
| 2014/0336752 A1* | 11/2014 | Ginn | A61F 2/01 623/2.11 |
| 2017/0105743 A1 | 4/2017 | Vale et al. | |

FOREIGN PATENT DOCUMENTS

WO 2014188300 A1 11/2014

\* cited by examiner

*Primary Examiner* — Laura A Bouchelle

(74) *Attorney, Agent, or Firm* — Greenberg Traurig, P.A.; Stephen G. Anderson

(57) ABSTRACT

A balloon sheath and associated methods are provided. An alternative embodiment comprising a sheath having a flaring end and associated methods are also provided.

1 Claim, 3 Drawing Sheets

BALLOON SHEATH AND ASSOCIATED METHODS

CROSS-REFERENCE TO RELATED APPLICATION

This application claims the benefit of, and priority to, U.S. Provisional Patent Application Ser. No. 62/576,147, filed Oct. 24, 2017, the entirety of which is incorporated by reference and commonly owned.

FIELD OF THE INVENTION

The present invention generally relates to expandable sheaths and associated methods.

SUMMARY OF THE INVENTION

It has been found that a balloon sheath is needed for procedures in which suction is applied within the body passageway. Such a balloon sheath includes a suction member that extends forward from the balloon portion of the sheath.

BRIEF DESCRIPTION OF THE DRAWINGS

Embodiments of the invention are described by way of example with reference to the accompanying drawings in which.

DETAILED DESCRIPTION OF EXAMPLE EMBODIMENTS

Figures 1, 2, 3:
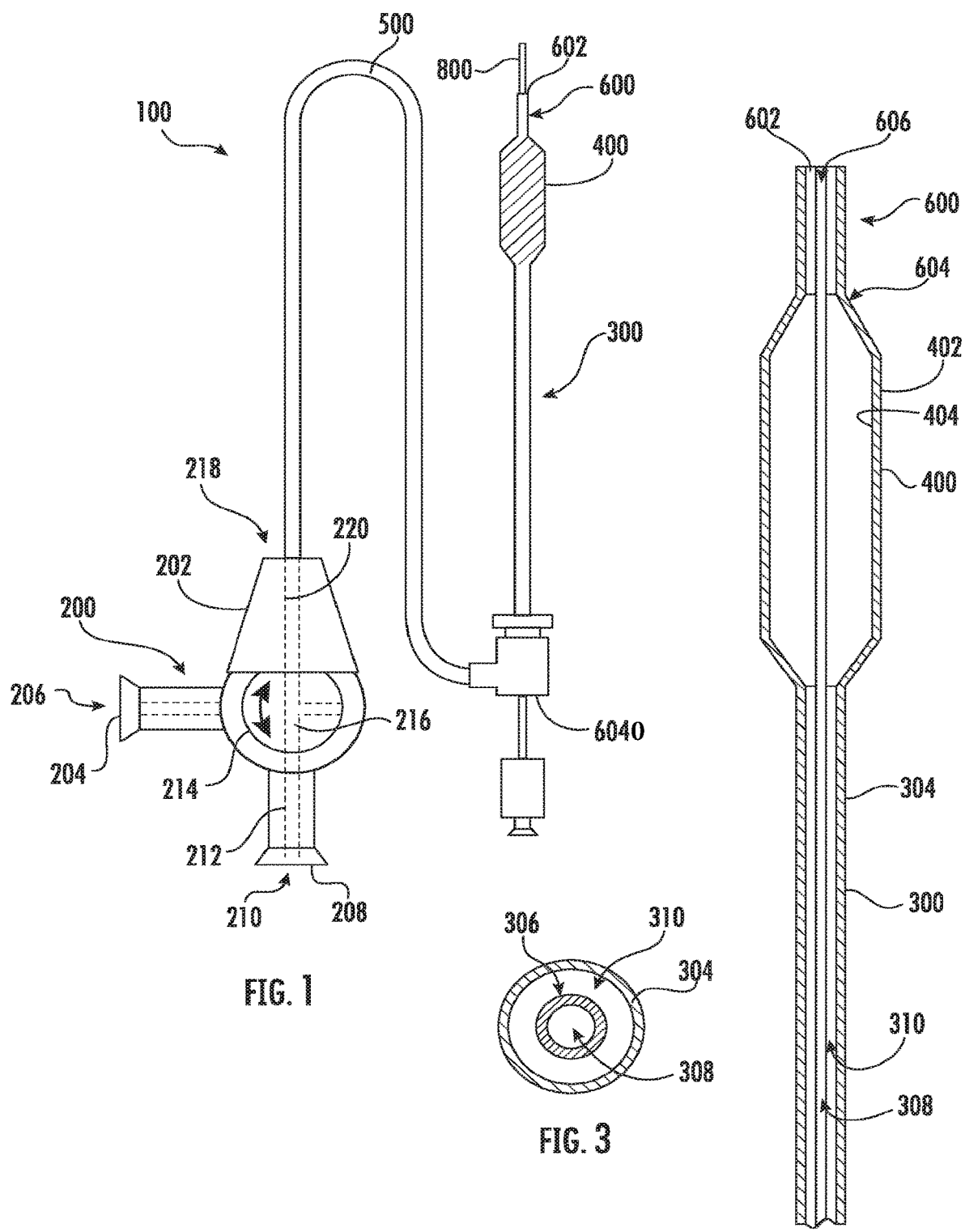
FIG. 1 is an example of the balloon sheath system with the dashed lines showing hidden features within the manifold.
FIG. 2 is a sectional view of the tubular shaft and balloon member.
FIG. 3 is a sectional view of the tubular shaft showing the first and second lumens.

Examples of possible configurations of the balloon sheath will now be discussed in more detail by referring to the drawings. The examples depicted in the drawings and described below are provided for the purpose of illustration and are not intended to disclose all possible configurations or examples or limit the scope of possible configurations or examples.

Referring to FIGS. 1-3, a sheath system 100 of the present disclosure includes a manifold 200 and a balloon sheath 300 comprising a balloon member 400 and a suction member 600.

The manifold includes a rigid body 202 having a first port 204 defining a first port opening 206 and a second port 208 defining a second port opening 210. These openings 206, 210 lead to respective fluid passages 212 within the rigid body 202. The fluid passages 212 extend to a valve 214.

The valve 214 allows the user to direct fluid into or out of the balloon sheath 300 from either of the first port 204 and/or second port 208 via a flexible tube 500. The valve 214 includes a valve passage 216 forming an opening through the valve 214. The valve 214 may be rotated as indicated by the arrows to provide fluid communication with the desired fluid passage 212.

A distal end 218 of the manifold 200 includes a distal passage 220 through the rigid body. The balloon sheath 300 is in fluid communication with the distal passage 220.

The first port 204 and second port 208 may be attached to external instruments such as a fluid source and/or a suction source. By connecting a fluid source to one of the first port 204 or second port 208, fluid may be supplied to the balloon member 400 for inflation or removed from the balloon member 400 for deflation. Accordingly, the fluid source generally functions as an inflation/deflation mechanism for the balloon member 400. In another embodiment, the balloon member 400 may be inflated and/or deflated via a first terminal end 6040 of the balloon sheath 300.

By connecting a suction source to one of the first port 204 or second port 208, suction may be provided to the suction member for providing suction via the suction tip 602. Alternatively, suction may be provided via the first terminal end 6040.

The manifold 200 may be made from any conventional surgically acceptable materials such as, for example, a surgically acceptable plastic or the like.

As depicted in the embodiment of FIG. 1, the balloon sheath 300 is connected to the manifold 200 at the distal end 218 of the manifold 200 via a flexible tube 500. The balloon sheath 300 extends from the distal end 218 of the manifold 200 to a distal end 302 of the tubular shaft 300 where the suction member 600 is located.

The balloon sheath 300 may be a flexible hollow polymeric material with an outer diameter small enough to fit within a circulatory system passageway such as an artery, vein, or vessel. The outer diameter of the balloon sheath 300 is defined by an outer wall 304.

In one embodiment, the balloon sheath 300 includes two fluid passages: one for supplying fluid pressure to the balloon and one for providing suction to the suction member 600. As shown in FIG. 3, these two fluid passages may be provided by including a smaller outer diameter tube 306 within the balloon sheath 300. The lumen of the smaller tube 306 defines a suction passage 308 that provides suction communication from the manifold 200 to the suction tip 602. The lumen of the tubular shaft 300 defines a balloon fluid passage 310 from the manifold 200 to the balloon member 400. It will be appreciated by one of ordinary skill in the art that other means of inflating the balloon member 400 may be utilized, including but not limited to those employed with existing balloon catheters.

The balloon member 400 may be annular shaped and has an interior wall 404 and an exterior wall 402. The balloon member 400 may be made from resilient polymeric material that can be inflated and deflated such as used in conventional balloon catheters and the like. When positive fluid pressure is supplied to the balloon member 400 via the balloon fluid passage 310, the balloon member 400 inflates, causing the outer wall 402 to expand. Likewise, when negative fluid pressure is supplied to the balloon member 400 via the balloon fluid passage 310, the balloon member 400 deflates, causing the outer wall 402 to contract.

When inflated, the outer wall 402 contacts the wall of the blood passage in which it is positioned. This effectively clogs the blood passage so that blood cannot substantially get past the balloon member 400 while the suction member 600 is operational.

The suction member 600 is positioned a distance forward the balloon member 400 and extends from a suction member proximal end 604 attached to the balloon member to the suction tip 602. The suction member 600 is a second tubular shaft that includes a suction member passage 606 that is in fluid communication with the suction passage 308. The suction member 600 may be made of a material, such as plastic, metal, or the like that will not collapse upon suction.

Figure 4:
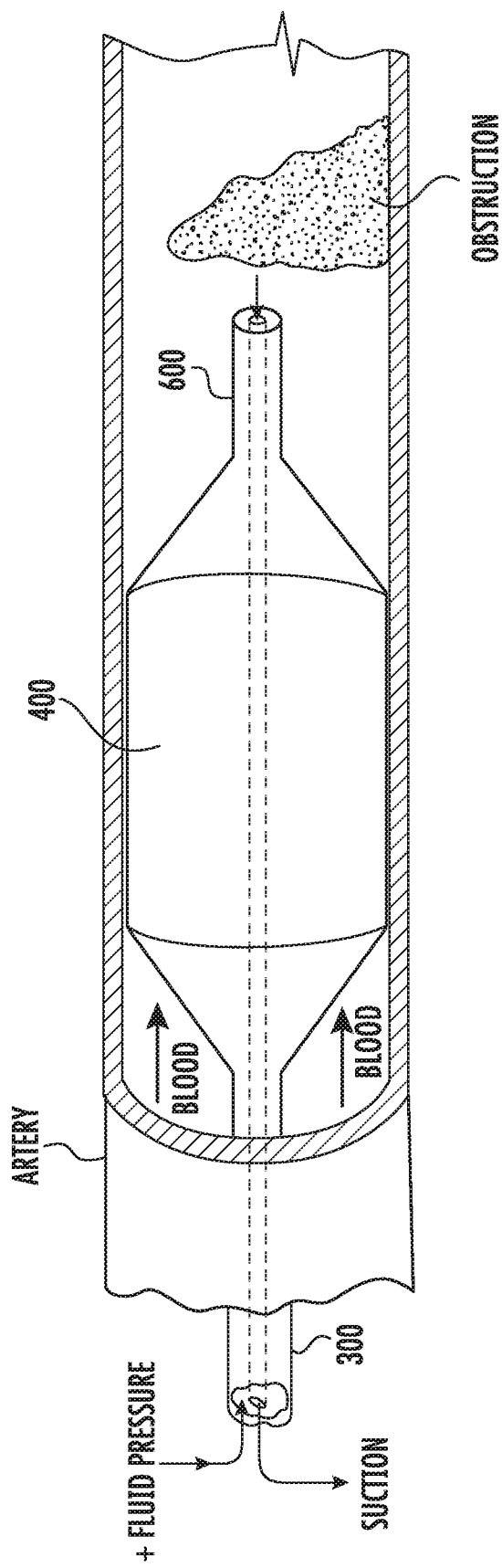
FIG. 4 is a sectional view of an artery showing the forward section of the balloon sheath performing a medical procedure.

An example of how the sheath system 100 may be used in a surgical procedure is now described by referring to FIG. 4. The balloon sheath 300 is inserted into a patient's artery and fluid pressure is applied to the balloon member 400 so that it inflates and contacts the artery wall, which substantially stops and/or reduces blood flow. While the balloon member 400 is inflated, suction is applied to the suction member 600 so that an obstruction in the artery can be removed via the suction member passage 606.

After the obstruction is removed, negative fluid pressure is applied to the balloon member 400 causing it to deflate. The balloon sheath 300 may then be removed from the blood vessel.

The balloon sheath 300 herein described may be used in conjunction with any suitable system, and therefore its use is not intended to be limited to the exemplary system 100. Moreover, the mechanism for inflating the balloon member 400 is not intended to be limited to the inflation/deflation process described, and it will be appreciated that alternative mechanisms may be utilized to achieve the same result. For example, the balloon member my expand by any suitable mechanical means, including but not limited to the use of a magnetically-controlled tension member that expands upon removal of an associated dilator 800 having magnetic properties complementary to that of the balloon member 400 and/or balloon sheath 300. The sheath system 100 may also be used to perform other types of surgical procedures besides the examples described herein. For example it may be used to treat ureteric obstructions in the urinary tract or obstructions in the sinuses. The balloon sheath 300 as herein described may also be used to quickly stop bleeding in an injured patient by inserting the balloon sheath 300 proximate a wound and expanding the balloon member 400.

Figure 5:
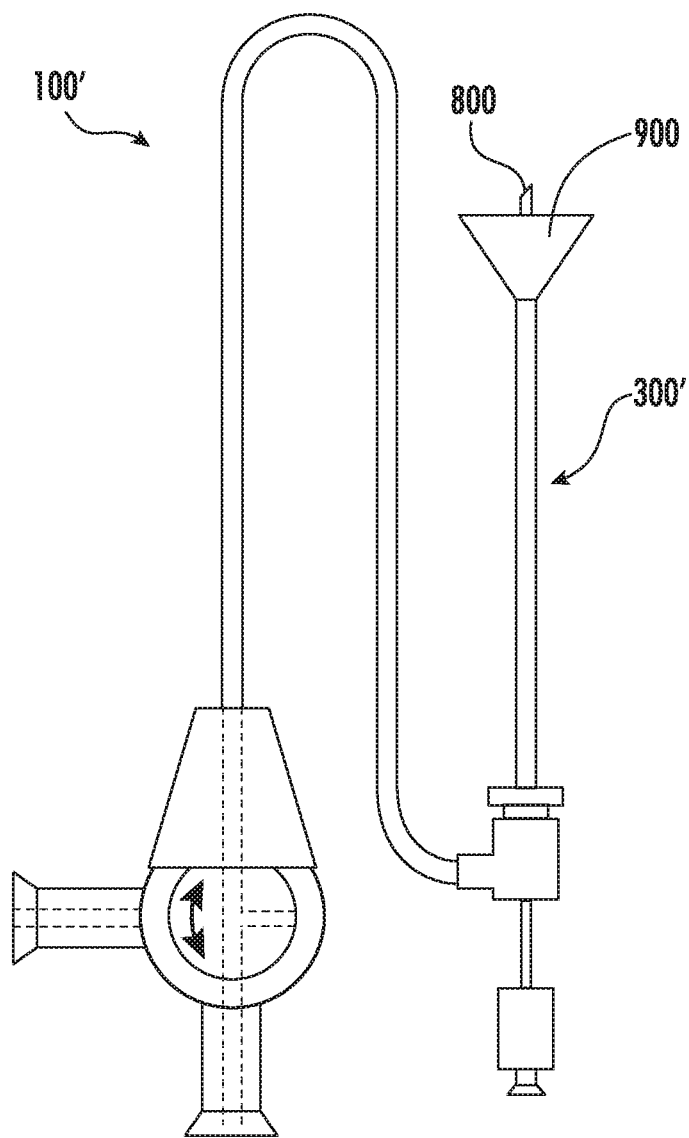
FIG. 5 is an example of a sheath of the present disclosure having a flared tip.

An alternative embodiment of the invention disclosed herein is depicted in FIG. 5. In this embodiment, the sheath 300' comprises a flaring member 900 at its terminal end. The flaring member 900 may open and close (or flare) via any suitable mechanical means, including but not limited to the use of a magnetically-controlled tension member that expands upon removal of a magnetized dilator 800. Suction may be applied to the flaring member 900 as described herein above to remove an obstruction from a circulatory system. The sheath 300' may be used in conjunction with the system 100 as herein described, however it is also envisioned that the sheath 300' may also be used with any other suitable system, including but not limited to a suitable known balloon catheter system and the like.

One exemplary method of use of the alternative sheath 300' includes a method for removing an obstruction within a circulatory system, the method comprising:
  i. inserting the sheath 300' into a circulatory system adjacent an obstruction;
  ii. expanding the end of the sheath 300';
  iii. passing a balloon catheter through the sheath 300' and the obstruction;
  iv. expanding a balloon portion of the balloon catheter within the circulatory system and beyond the obstruction; and
  v. simultaneously applying suction to the sheath 300' and pulling the catheter so as to pull the obstruction into the sheath 300'.

This disclosure describes possible examples, configurations, and uses of the sheath system 100, but not all possible examples, configurations, or uses. Where a particular feature is disclosed in the context of a particular example, that feature can also be used, to the extent possible, in combination with and/or in the context of other examples. The catheter may be embodied in many different forms and should not be construed as limited to only the examples described here.

Although the invention has been described relative to various selected embodiments herein presented by way of example, there are numerous variations and modifications that will be readily apparent to those skilled in the art in light of the above teachings. It is therefore to be understood that, within the scope of the claims hereto attached and supported by this specification, the invention may be practiced other than as specifically described.

What is claimed is:
1. A balloon sheath comprising:
  a first end, a second end, and a tubular portion therebetween, the tubular portion defining a suction passage extending lengthwise therethrough and a balloon member positioned circumferentially about a portion of the suction passage and defining a balloon fluid passage, the balloon fluid passage being in fluid communication with the suction passage;
  wherein at least one of the first and second ends is magnetized and expands upon removal of a magnet of opposite polarity.

* * * * *